United States Patent [19]

Vargas et al.

[11] Patent Number: 4,594,964
[45] Date of Patent: Jun. 17, 1986

[54] METHOD AND APPARATUS FOR THE MASS REARING OF FRUIT FLIES

[75] Inventors: Roger I. Vargas, Honolulu, Hi.; Harold E. Mabry, McAllen, Tex.; Arthur L. Myers, Honolulu; Richard M. Kobayashi, Kaneohe, both of Hi.

[73] Assignee: United States of America as represented by the Secretary of Agriculture, Washington, D.C.

[21] Appl. No.: 696,222

[22] Filed: Jan. 29, 1985

[51] Int. Cl.[4] .............................................. A01K 67/00
[52] U.S. Cl. .......................................... 119/1; 119/15
[58] Field of Search ...................................... 119/1, 15

[56] References Cited

U.S. PATENT DOCUMENTS

| | | | |
|---|---|---|---|
| 3,893,420 | 7/1975 | Andreev et al. | 119/1 |
| 3,941,089 | 3/1976 | Andreev et al. | 119/1 |
| 4,411,220 | 10/1983 | Voegele et al. | 119/1 |
| 4,418,647 | 12/1983 | Hoffman | 119/1 |

OTHER PUBLICATIONS

L. F. Steiner and S. Mitchell, "Tephritid Fruit Flies," pp. 555–583, *Insect Colonization and Mass Production,* Ed. C. N. Smith, Academic Press, NY (1966).
D. J. Nadel, "Current Mass-Rearing Techniques for the Mediterranean Fruit Fly," pp. 13–18, Proceedings of Panel on *Sterile-Male Technique for Control of Fruit Flies,* IAEA, Vienna (1970).
N. Tanaka, "Artificial Egging Receptacles for Three Species of Tephritid Flies," *Journal of Economic Entomology* 58(1): 177–178 (1965).
N. Tanaka, R. Okamoto, D. L. Chambers, "Methods of Mass Rearing the Mediterranean Fruit Fly Currently Used by the U.S. Department of Agriculture," pp. 19–23, Proceedings of panel on *Sterile-Male Technique for Control of Fruit Flies, IAEA, Vienna (1970).*
R. I. Vargas, "Alternative Egg Collection System for Mass Production of Mediterranean Fruit Fly (Diptera: Tephritidae), *Journal of Economic Entomolgy* 77(4): 1064–1069 (1984).

Primary Examiner—Hugh R. Chamblee
Attorney, Agent, or Firm—M. Howard Silverstein; David G. McConnell; Margaret A. Connor

[57] ABSTRACT

An improved method and apparatus is disclosed for the mass rearing of fruit flies. The apparatus includes a cage for housing fruit flies; a tube extending inside the cage which has a solid bottom section for holding water to maintain a humidity inside the tube of at least 80% and a perforated section with a plurality of openings of a size and spacing which stimulate fly oviposition and maximize egg production; and means closing the ends of the tube. After oviposition, eggs are readily collected by flushing the tube with water.

12 Claims, 4 Drawing Figures

METHOD AND APPARATUS FOR THE MASS REARING OF FRUIT FLIES

BACKGROUND OF THE INVENTION

1. Field of the Invention

This invention relates to an improved method and apparatus for the mass rearing of insects, particularly fruit flies.

2. Description of the Art

Tephritid fruit flies (Diptera: Tephritidae) such as the Mediterranean fruit fly [*Ceratitis capitata* (Wiedemann)] commonly known as the medfly, the oriental fruit fly (*Dacus dorsalis* Hendel), the melon fly (*Dacus cucurbitae* Coquillett), the Caribbean fruit fly [*Anastrepha suspensa* (Loew)], the olive fruit fly (*D. oleae* Gmelin), and the Mexican fruit fly [*A. ludens* (Loew)] are among the worst pests of citrus, deciduous fruits, and vegetables and present a major threat to fruit and vegetable production in areas with mild winters.

Currently, the primary method of control of fruit flies is the extensive use of insecticides or insecticidal baits. The widespread broadcasting of insecticides has several disadvantages, notably, the development of insecticide resistance, the destruction of bees and desirable predators and parasites, and contamination of the environment. One alternative method of control is the release of large numbers of sterile male fruit flies which mate with the native female population resulting in the production of infertile eggs.

An important factor in the success of any sterile-insect release program is the ability to efficiently and economically mass produce the flies. The first step in the mass production of sterile Mediterranean fruit flies is the production of eggs. The most commonly used collection technique is the screen method. In this method a large cage having a synthetic cloth front screen panel is mounted on a monorail. The fruit flies are placed inside the cage in the pupal stage and when they emerge, they oviposit through the screen and the eggs drop into a trough of water located on the outside of the cage. The water prevents desiccation of the eggs. The screen method has been adapted most successfully at the Mediterranean Fruit Fly Mass Rearing Facility, Metapa, Mexico, to collect over one billion eggs per week. The primary disadvantage of this method is that many of the eggs get caught on the screen and desiccate completely or partially prior to dropping into the trough. Thus the viability and quality of the eggs are significantly reduced.

A second method of egg collection is oviposition into perforated polyethylene bottles held in openings in a cage. Subsequent to oviposition by the flies, the bottles are removed from the cages for collection of the eggs. The bottle method has been used primarily as a research tool and was first used on a large scale (over 200 million eggs per week) in 1980 for the California medfly infestation at the California/APHIS Mediterranean fruit fly facility in Honolulu. At this facility, about 120,000 adult flies are housed in cages ($41 \times 117 \times 107$ cm) made of 0.95-cm plywood with mesh screening at the top. Two circular openings are located on each side of a cage to receive opaque 1-liter, slightly tapered, cylindrical polyethylene, capped bottle containers having 300 holes (denoted as 0.3-mm diameter). A cellulose sponge saturated with water or fruit juice is placed in the container to provide ovipositional stimulus and prevent desiccation of the eggs. The flies oviposit through the holes into the bottles. The primary disadvantage of this method is the time consuming and labor intensive egg collection procedure which involves removing each container from the cage, uncapping the container, and washing out the eggs. Another disadvantage is the escape of flies from the cage when the containers are removed. A third disadvantage is the lack of amenability of this system to automation. The hundreds of bottles needed for collection of over 200 million eggs precludes both the use and automation of the bottle system for egg collection in a large scale mass production facility (over 1 billion eggs per week).

SUMMARY OF THE INVENTION

We have discovered an improved method and apparatus for collection of eggs for large scale production of fruit flies. Due to novel features of our invention, fruit flies are stimulated to lay 44% greater numbers of eggs over the screen method and 14% greater numbers of eggs over the bottle method, even when the parameters of hole size, spacing and number of holes have been optimized over the conventional bottle method as described in detail below. At a required mass production level of one billion eggs per week, 44% and 14% translates into 440 and 140 million eggs, respectively. With our method, loss of quality and viability of eggs, which was 26% less with the screen method, is minimized and labor to collect the eggs is reduced 70% from the bottle method. Because sponges are not required and water can flow freely through the tube, our method is suitable for application of automated sprinkler technology. Consequently, further reductions in labor are contemplated.

The apparatus of the invention comprises: (a) a cage for housing fruit flies; (b) a tube extending lengthwise inside the cage which is made of a material which does not adversely affect fly oviposition, the tube having a solid bottom section for holding sufficient water in the tube when the ends are closed to maintain a humidity in the tube of at least 80%, the tube having a perforated section with a plurality of openings large enough for fruit flies to oviposit through, small enough so that excessive water does not flow out of the openings when the tube is flushed with water to collect the oviposited eggs, and of a size such that when the humidity in the tube is 80–100%, water evaporates out of the openings at a rate which causes the flies to be attracted to the openings and stimulated to oviposit, the spacing of the holes being close enough to maximize egg production and far enough apart to provide resting space for the flies; and (c) means for closing the ends of the tube.

In the method of the invention, fruit flies are placed in a cage which contains one or more tubes having the features described above. The tube is capped at one end and sufficient water is placed in the tube to provide a humidity of at least 80% after the other end is closed. The flies oviposit through the openings into the tube and after oviposition, the eggs are readily collected by flushing the eggs from the tube into a collection receptacle.

In accordance with this discovery, it is an object of the invention to provide an efficient, labor saving, and economical system for the large-scale rearing of fruit flies.

It is also an object of the invention to provide an improved fruit fly rearing system suitable for automation.

Another object of the invention is to provide a fruit fly rearing system in which flies are stimulated to oviposit.

A further object of the invention is to rear Tephritid fruit flies in a manner which facilitates their recovery for mass release into the environment.

Other objects and advantages of the invention will become readily apparent from the ensuing description.

DESCRIPTION OF THE PREFERRED EMBODIMENTS

A critical parameter in the mass rearing of fruit flies is the provision of a cage having a surface area per number of flies large enough to provide sufficient resting and mating space, to provide room for food required for maximum egg production, to avoid build up of excessive metabolic heat (i.e., that amount which would lower egg production), and not so large as to waste space. The cage must contain a screened portion sufficient to allow entry of air necessary for the flies.

A critical feature for rearing fruit flies in accordance with the instant invention is the provision within the cage of a tube or plurality of tubes having features which stimulate fruit flies to oviposit so that egg production is increased over the conventional methods which provide a humidity of 80-100% in the area where the eggs are held after oviposition and prior to collection so that desiccation of the eggs is reduced and the viability and quality of the eggs is increased over conventional mass rearing methods; and which provide for ready egg collection.

Figure 4:
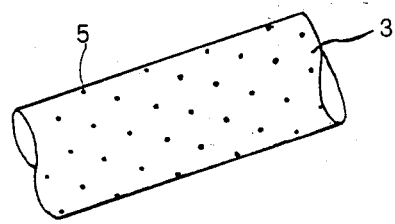
FIG. 4 is an enlarged, partial view of the tube shown in FIG. 3.

The features of the tube required to accomplish this are a solid bottom section of a size sufficient to hold water such that when the ends of the tube are closed the humidity in the tube is 80-100%, and a perforated section having a plurality of openings which are large enough for fruit flies to oviposit through, small enough so that excessive water does not flow out of the openings when the tube is flushed with water to collect the eggs, and of a size such that when the humidity in the tube is 80-100%, water evaporates out of the openings at a rate which causes the flies to be attracted to the openings and stimulated to oviposit. We have found that the critical hole size opening which accomplishes this is about 0.75-1.5 mm in diameter and preferably about 1 mm in diameter. The spacing of the holes should be close enough to maximize egg production and far enough apart to provide space for the ovipositing flies. For the Mediterranean fruit fly, the oriental fruit fly, and the melon fly, the critical spacing to accomplish this is between about 0.5 and 1.5 cm and preferably about 1.0 cm. To maximize the area around each opening for flies to land on without crowding, it is preferred that the spacing between one opening and the six nearest openings be equidistant as shown in FIG. 4. The number of openings should be that which maximizes mass rearing of fruit flies without overcrowding the flies or generating excessive metabolic heat. We have found that the preferred number of openings is 3200-4000 per 45,000-75,000 female flies and more preferably per 60,000 female flies where the flies are housed in the cage in a 1:1 sex ratio.

The diameter of the tube should be large enough to hold sufficient water to provide the required humidity and small enough so the tube is attractive to the flies. Another critical feature is that the tube be fabricated of a material which does not adversely affect fly oviposition. Such materials include polyvinyl chloride, polyethylene, and polypropylene. The wall thickness of the tube is not critical as long as it is not so thick as to prevent oviposition through the openings by the flies.

Figure 1:
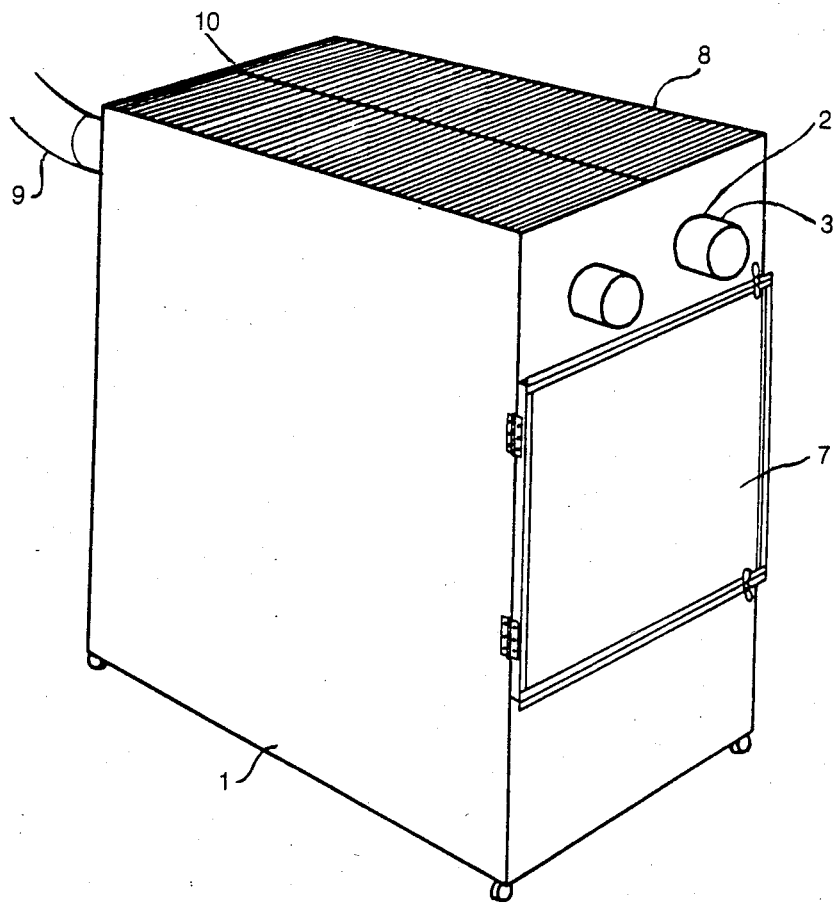
FIG. 1 is a perspective view of the apparatus of the invention.
Figure 2:
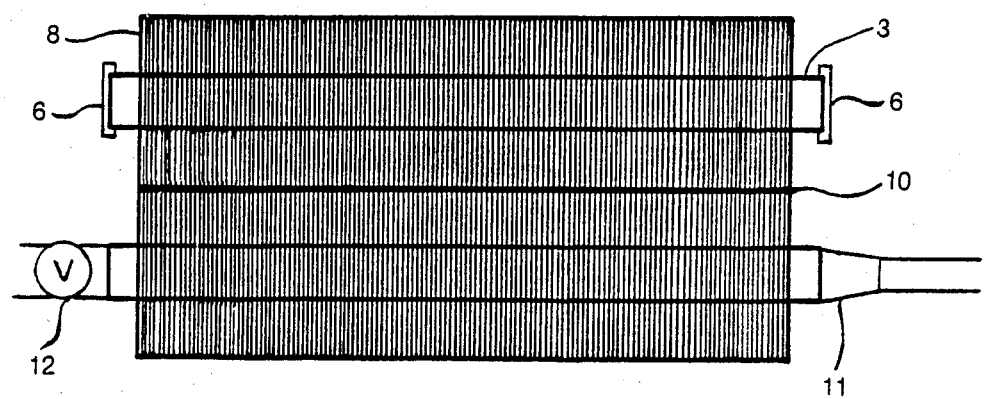
FIG. 2 is a top plan view of the apparatus shown in FIG. 1.
Figure 3:
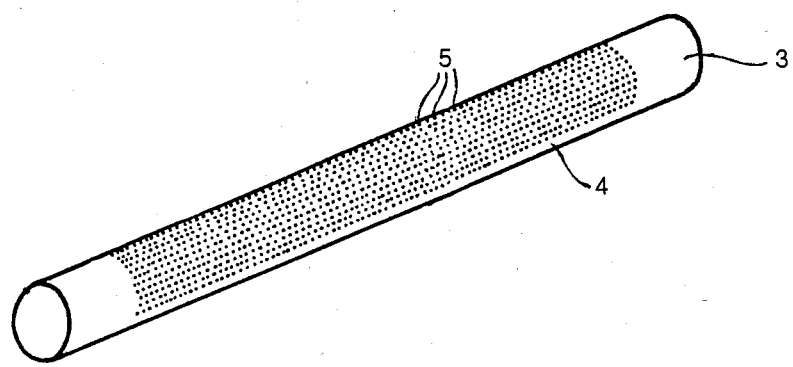
FIG. 3 is a perspective view of the tube used in the invention.

The apparatus of the invention is next described with reference to FIGS. 1-4. Cage 1 has openings 2 to hold tubes 3 in the cage. Tubes 3 have a solid bottom section 4 for holding water and a perforated segment with a plurality of openings 5 for fly ovipositing. Removable caps 6 fit on the ends of tubes 3 to close tube 3. Door 7 allows for the placement of the flies into cage 1. As shown in the embodiment of FIG. 1, the upper surface is screen 8. Removable hose 9 which attaches to a source of water at one end and to tube 3 at the other is used to fill tube 3 with sufficient water to provide a humidity in the tube of at least 80% and after egg production, is used to flush the eggs from the tube into a collection receptacle.

We have found that a rectangular cage which is 58.4 cm wide × 118.1 cm high × 118.1 cm long and divided into two compartments by screen 10 meets all the critical parameters outlined about when housing about 120,000 flies per compartment in a sex ratio of 1:1, and is a convenient size for the mass rearing of fruit flies. It should be noted that other size cages which meet the critical requirements are contemplated by the invention. The cage may be made of any rigid material such as metal or wood. Metal is preferred due to its resistance to termites and wood rot.

Tube 3 is placed to extend lengthwise in each compartment as shown in FIG. 1. The critical size, spacing, and number of openings in tube 3 are as previously described. In the size cage described above, it is preferred that the diameter of tube 3 be about 7.6-12.7 cm and more preferably about 10.2 cm. The solid bottom section of the tube holds sufficient water to provide 80-100% humidity in the tube and maximize the surface area allowable in the perforated segment. When the screening portion of cage 1 is located on the top as shown in FIG. 1, it is preferred that tube 3 be located in a position, measured from the uppermost portion of the cage, which is between 1/5 and ⅓ of the vertical distance between the uppermost portion and the lowest portion of the cage.

In use, fruit flies in the pupal stage, are placed in cage 1. One end of tube 3 is capped and the tube is filled with sufficient water to provide a humidity in the tube of at least 80% after the other end is capped. The fruit flies are held for a time and at a temperature, humidity, and lighting conditions suitable for oviposition. The humidity in the tube in combination with the critical opening size causes the water in the tube to evaporate out of the openings in the tube at a rate which causes the fruit flies to be attracted to the openings and stimulated to oviposit. The eggs accumulate in the tube where they are held until collection. Because the humidity in the tube is 80-100%, loss of viability and quality of the eggs from desiccation is avoided. Next the end caps are removed and tube 3 flushed with water at a rate sufficient to wash the eggs out of the tube into a collection receptacle. If desired, tube 3 can be covered during the preoviposition period to prevent plugging of the holes by fly waste or tracking of food.

When automation is desired, caps 6 can be replaced at one end by a nozzle 11 for filling and flushing tube 3 and at the other end by valve 12 for opening and closing the tube. It is also within the compass of the invention that oviposition stimulating compounds be used, as desired, with the method and apparatus of the invention.

EXAMPLE

The method and apparatus of the invention are next described in further detail in the following illustrative examples.

EXAMPLE 1

In the following example, the egg production using the method and apparatus of the invention was compared to production using bottles prepared by the instant inventors wherein the oviposition hole size, hole spacing, and number of oviposition holes were optimized in accordance with the parameters of the invention.

Referring to FIG. 1, cage 1 was made of sheet metal on the sides and bottom and covered on the top with a plastic screen (40.6 mesh per cm. The dimensions of the cage were 58.4×118.1×118.1 cm and it was divided lengthwise into two equal compartments by screen 9 having a mesh size of 7 squares per cm. Tube 3 was located midway in the width of one compartment and at a height of 100 cm from the lowest point of the cage. Tube 3 which was fabricated of colorless, opaque polyvinyl chloride had a diameter of 10.2 cm and a length of 120 cm and had 4000 1-mm openings along the sides and top of the tube inside the cage at an equidistant spacing of 1.0 cm. The solid section of tube was about 15% of the circumference. A portion of tube 3 without openings extended outside of cage 1 at either side for ready capping with caps 6.

Bottles having optimized hole spacing, hole size, and number of holes were used for comparison. Ten 1-liter colorless, opaque polyethylene bottles, each perforated with 400 1-mm diameter holes, spaced at equidistant 1.0 cm intervals, were placed in the second compartment of cage 1 at the same height as tube 3. This arrangement presented the flies with an equal number of oviposition holes in each compartment. A 2.5×2.5×10-cm cellulose sponge saturated with water was used in each perforated bottle to provide an ovipositional stimulus and prevent desiccation of the eggs.

Into each compartment were placed about 60,000 female and 60,000 Mediterranean fruit flies in the pupal stage. Adults were maintained on a 3:1 volumetric mixture of sugar and ICN enzymatic yeast hydrolysate (U.S. Biochemical Corp., Cleveland, OH.). The double-compartment cage was kept in a room maintained at 24.5+° C. and 70+10% relative humidity. The photoperiod regime was 12:12 (LD) on days 1 to 3; 24:0 (LD) on days 4 to 14. On day 4, the saturated sponges decribed above were placed in the bottles and water placed in tube 3 sufficient to provide a humidity of at least 80%.

For a standard 10-day collection period, the mean number of eggs collected was 53.4 ml/day for the method of the invention and 46.0 ml/day for the bottle method, indicating an increase in egg production of 14% for the method of the invention over the bottle method. These values were significantly different at a 5% level of probability (analysis of variance and Duncan's multiple range test).

EXAMPLE 2

The procedure described in Example 1 was also used to measure and compare labor time for egg collection for each method. Removal of eggs from the bottles required the following steps: (1) unscrewing caps from the ten bottles, (2) removing and rinsing the sponges inside each bottle, flushing the eggs from each bottle into a collection trough using a hose with a fine mist nozzle, (4) draining water and eggs from the trough into a collection receptacle, and (5) replacing the sponges in the bottles and securing the caps. Removal of eggs from the tube required the following steps: (1) unsnapping the caps from each end of the tube, (2) flushing the eggs from the tube into a collection receptacle using a hose with a fine mist nozzle, and (3) replacing the caps.

Based on ten trials, the mean time for one person to remove the eggs from the tube was 1.5 min, compared with 5 min for the bottles, a reduction in labor time of 70%.

It is understood that the foregoing detailed description is given merely by way of illustration and that modification and variations may be made therein without departing from the spirit and scope of the invention.

Having thus described the invention, we claim:

1. An improved apparatus for the mass rearing of Tephritid fruit flies, comprising:
   (a) a cage for housing fruit flies having openings for holding a tube;
   (b) a tube extending lengthwise inside said cage which is made of a material which does not adversely affect fly oviposition, said tube having a solid bottom segment for holding sufficient water in said tube when the ends of said tube are closed to maintain a humidity in said tube of at least 80%, said tube having a perforated segment with a plurality of openings large enough for fruit flies to oviposit through, small enough so excessive water does not flow out of the openings when said tube is flushed with water, and of a size such that when the humidity in said tube is 80–100%, water evaporates out of said openings at a rate which causes the flies to be attracted to said openings and stimulated to oviposit, the spacing of said openings being close enough to maximize egg production and far enough apart to provide resting space for the flies; and
   (c) means for opening and closing the ends of said tube.

2. The apparatus of claim 1 further comprising means for flushing fruit fly eggs out of the inside of said tube.

3. The apparatus of claim 1 wherein said openings in said tube are about 0.75–1.5 mm in diameter.

4. The apparatus of claim 2 wherein said openings in said tube are spaced at a distance of about 0.5–1.5 cm.

5. The apparatus of claim 4 wherein the spacing of said openings is equidistant.

6. The apparatus of claim 2 wherein said tube has a diameter of about 7.6–12.7 cm.

7. The apparatus of claim 2 wherein said flushing means is automated.

8. An improved method for the mass rearing of Tephritid fruit flies, comprising placing the flies in a cage, said cage having a tube extending lengthwise inside said cage which is made of a material which does not adversely affect fly oviposition, said tube having a solid bottom segment for holding sufficient water in said tube when the ends of said tube are closed to maintain a humidity in said tube of at least 80%, said tube having a perforated segment with a plurality of openings large enough for fruit flies to oviposit through, small enough so excessive water does not flow out of the openings when said tube is flushed with water, and of a size such that when the humidity in said tube is 80–100%, water evaporates out of said openings at a rate which causes the flies to be attracted to said openings and stimulated to oviposit; the spacing of said openings being close enough to maximize egg production and far enough apart to provide resting space for the flies; adding water to said tube to provide a humidity inside said tube of at least 80%; closing the ends of said tube; holding the cage for a time and at a temperature, humidity, and lighting conditions suitable for oviposition of the flies through the openings in said tube; opening the ends of said tube; and flushing the eggs out of said tube.

9. The method of claim 8 wherein said openings in said tube are about 0.75–1.5 mm in diameter.

10. The method of claim 8 wherein said openings in said tube are spaced at a distance of about 0.5–1.5 cm.

11. The method of claim 10 wherein the spacing of said openings is equidistant.

12. The method of claim 8 wherein said tube has a diameter of about 7.6–12.7 cm.

* * * * *

UNITED STATES PATENT AND TRADEMARK OFFICE
CERTIFICATE OF CORRECTION

PATENT NO. : 4,594,964

DATED : June 17, 1986

INVENTOR(S) : Roger I. Vargas et al.

It is certified that error appears in the above—identified patent and that said Letters Patent is hereby corrected as shown below:

In col. 3, line 35, after the word "methods", insert -- ; --.

In col. 5, line 53, after "60,000", insert -- male --.

In col. 5, line 58, delete "24.5+°C" and insert -- 24.5°C --.

In col. 5, line 58, delete "70+10%" and insert -- 70±10% --.

In col. 5, line 27, after "cm", insert -- ) --.

Signed and Sealed this

Second Day of December, 1986

*Attest:*

DONALD J. QUIGG

*Attesting Officer*     *Commissioner of Patents and Trademarks*